United States Patent
Takasaki

(10) Patent No.: US 8,345,092 B2
(45) Date of Patent: Jan. 1, 2013

(54) IMAGING APPARATUS AND ENDOSCOPE

(75) Inventor: Kosuke Takasaki, Miyagi (JP)

(73) Assignee: FUJIFILM Corporation, Tokyo (JP)

( * ) Notice: Subject to any disclaimer, the term of this patent is extended or adjusted under 35 U.S.C. 154(b) by 625 days.

(21) Appl. No.: 12/563,872

(22) Filed: Sep. 21, 2009

(65) Prior Publication Data

US 2010/0073470 A1    Mar. 25, 2010

(30) Foreign Application Priority Data

Sep. 22, 2008  (JP) ................... 2008-242837

(51) Int. Cl.
*H01L 23/28* (2006.01)
*H01L 23/31* (2006.01)

(52) U.S. Cl. .......................... 348/76; 257/680
(58) Field of Classification Search ............. 348/76; 257/680, 431, 460
See application file for complete search history.

(56) References Cited

U.S. PATENT DOCUMENTS

| | | | |
|---|---|---|---|
| 6,873,034 B2 * | 3/2005 | Nakamura et al. | 257/680 |
| 6,933,172 B2 * | 8/2005 | Tomimatsu | 438/109 |
| 7,070,748 B2 * | 7/2006 | Unehara et al. | 423/338 |
| 7,180,007 B2 * | 2/2007 | Nishikawa et al. | 174/257 |
| 2003/0155639 A1 * | 8/2003 | Nakamura et al. | 257/680 |
| 2005/0017373 A1 * | 1/2005 | Nishikawa et al. | 257/778 |

FOREIGN PATENT DOCUMENTS

| | | |
|---|---|---|
| JP | 5-207971 A | 8/1993 |
| JP | 6-178757 A | 6/1994 |
| JP | 2001-46323 A | 2/2001 |
| JP | 2002-159438 A | 6/2002 |
| JP | 2002-159439 A | 6/2002 |

* cited by examiner

*Primary Examiner* — Khanh Dinh
(74) *Attorney, Agent, or Firm* — Sughrue Mion, PLLC

(57) ABSTRACT

An imaging apparatus includes an observation optical system, a solid state imaging element photoelectrically converting an image from the observation optical system, a flexible board electrically connected to the solid state imaging element, a plurality of electronic components and a plurality of signal cables electrically connected to the flexible board, and a first resin sealing the electronic components and a second resin sealing a connection part of the signal cables. A thixotropic ratio of the first resin is set to be lower than a thixotropic ratio of the second resin. Accordingly, apparatus and an endoscope, which can be made compact, and have high physical and electrical reliability without increasing a size of the imaging apparatus, are provided.

10 Claims, 5 Drawing Sheets

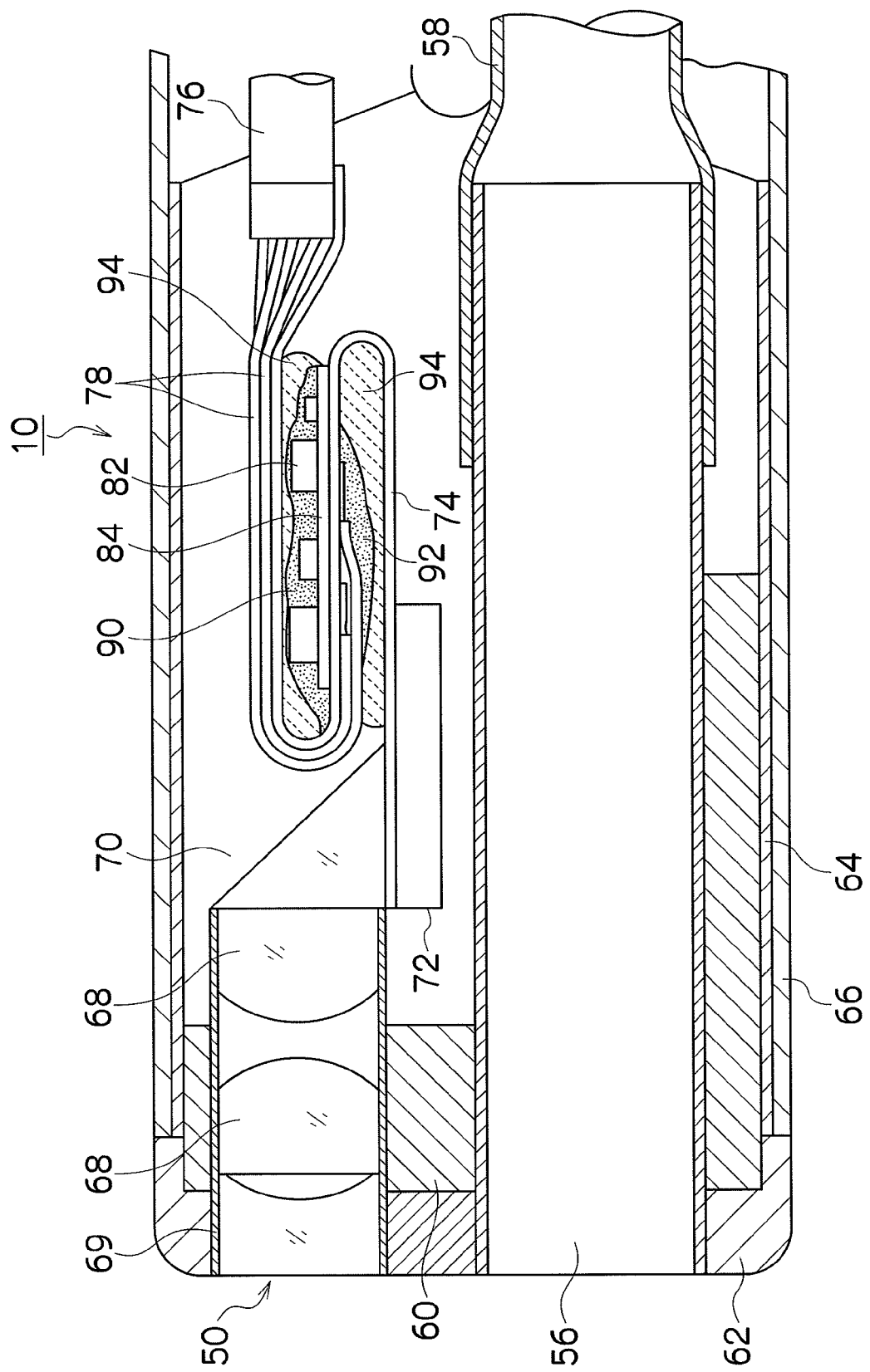

ively, in the imaging apparatus for an endoscope, there is the problem that unless the physical property, coating method and the like of a resin are properly selected, the resin cannot be favorably filled even if the circuit board and the cable connection part are sealed with the resin, and voids and the like occur to cause reduction in physical and electrical reliability.
IMAGING APPARATUS AND ENDOSCOPE

BACKGROUND OF THE INVENTION

1. Field of the Invention

The present invention relates to an imaging apparatus and an endoscope, and particularly to a compact imaging apparatus in which electronic components and signal cables are connected to a bendable circuit board, and an endoscope.

2. Description of the Related Art

An endoscope includes an insertion section which is inserted into a body of a test subject, and an observation optical system configured by a lens and a prism is provided at a tip end portion of the insertion section. A solid state imaging element such as a CCD is provided at an image forming position of the observation optical system. The solid state imaging element is connected to a multicore cable through a flexible board with flexibility. Further, electronic components are mounted on the flexible board to drive the solid state imaging element. The multicore cable is electrically connected to a processor. Thereby, the observational image of a lesion portion or the like is formed on the imaging element through the observation optical system, and is subjected to photoelectric conversion, and then, the electric signal of it is properly subjected to signal processing by a processor, is output to a monitor TV, and the observational image is displayed on the monitor TV.

Incidentally, the tip end portion of the insertion section of an endoscope is desired to have a small diameter for the purpose of reduction in burden on a test subject. Therefore, the wiring module such as a board is desired to be compact (reduction in diameter/reduction in length, in concrete). Therefore, an increase in the elements on the circuit board, reduction in pitch of the pattern on the circuit board, reduction in diameter of a cable, and space saving of the cable connection part are required.

Further, since a sealing resin used in an endoscope not only satisfies the bonding strength and electric performance, but also needs to meet specifications for cleaning after use, the sealing resin is required to have water-tightness and air-tightness, and sealing needs to be performed with a minimum of voids.

Concerning resin sealing of the imaging apparatus for an endoscope, various proposals are made.

For example, Japanese Patent Application Laid-Open No. 05-207971 describes an endoscope in which an inside of a frame of an outer circumference is filled with a first resin for reinforcing the imaging apparatus, and a second resin for ensuring flexibility of the rear end portion of the imaging section.

Japanese Patent Application Laid-Open No. 2002-159438 describes an imaging unit for an endoscope in which a resin is injected and filled with high density by providing a frame for autoclave resistance.

Japanese Patent Application Laid-Open No. 2001-46323 describes an endoscope in which after sealing is performed with a fluorine rubber resin, its periphery is sealed with an epoxy resin with relatively high water absorptivity, and the epoxy resin is covered with a tube, for autoclave resistance.

Japanese Patent Application Laid-Open No. 2002-159439 describes an endoscope in which an inside of a frame or a heat-shrinkable tube, which is provided outside, is sealed with a first adhesive agent which ensures insulation, and an outside of the first resin is sealed with an adhesive agent with low steam permeability.

Japanese Patent Application Laid-Open No. 06-178757 describes an endoscope in which a flexible board mounted with electronic components is bent to have a steric structure, and the electronic components, a tip end portion of the flexible board and a cable connection part are sealed with a resin.

SUMMARY OF THE INVENTION

Incidentally, in the imaging apparatus for an endoscope, there is the problem that unless the physical property, coating method and the like of a resin are properly selected, the resin cannot be favorably filled even if the circuit board and the cable connection part are sealed with the resin, and voids and the like occur to cause reduction in physical and electrical reliability.

In each of Japanese Patent Application Laid-Open No. 05-207971 and Japanese Patent Application Laid-Open No. 2002-159438, a frame is provided at an outer circumference of the imaging section, and a resin is filled in the frame, whereby the structure which is easily filled is made. Especially in Japanese Patent Application Laid-Open No. 2002-159438, voids can be decreased by injection filling. However, by providing a frame, there arises a problem that the cost of the components increases, and the diameter of the circumference of the imaging section becomes thick.

In each of Japanese Patent Application Laid-Open No. 2001-46323 and Japanese patent Application Laid-Open No. 2002-159439, a certain kind of resin is coated to seal the circuit board and the cable connection part without using a frame. However, since the physical property of the resin is not properly selected, the resin cannot be favorably filled, and there is the fear of causing voids and the like. Thus, there is the problem of reducing reliability. In addition, when the cable is reduced in diameter, coating is frequently made of a fluorine resin in general, and there arises the problem that the control of the coating range is difficult.

Japanese Patent Application Laid-Open No. 06-178757 describes use of a resin in accordance with each step in the stage of assembly, but does not describe the concrete property of the resin. Therefore, there arises the problem that the resin cannot be filled favorably, voids and the like occur, and physical and electrical reliability are reduced.

The present invention is made in view of the above circumstances, and has an object to provide an imaging apparatus and an endoscope with high physical and electrical reliability without increasing the size of the imaging apparatus.

In order to attain the above-described object, an imaging apparatus according to an aspect of the present invention includes: an observation optical system; a solid state imaging element which photoelectrically converts an image from the observation optical system; a bendable circuit board electrically connected to the solid state imaging element; a plurality of electronic components and a plurality of signal cables electrically connected to the bendable circuit board; a first resin which seals the electronic components; and a second resin which seals a connection part of the signal cables, the second resin having a thixotropic ratio which is higher than a thixotropic ratio of the first resin.

In the imaging apparatus, the first resin which seals the plurality of electronic components has a low thixotropic ratio, and therefore, has high flowability. As a result, the resin can be prevented from being unfilled, and occurrence of voids can be reduced. Further, the second resin which seals the connection part of the signal cables has a thixotropic ratio higher than that of the first resin, and therefore, flowability is suppressed. Thereby, the second resin can be prevented from flowing over the connection part along the signal cables. Thereby, the imaging apparatus with high physical and electrical reliability can be obtained without increasing the size of the imaging apparatus.

In the imaging apparatus according to the aspect of the invention, it is preferable that the plurality of signal cables are connected to the bendable circuit board in a state in which the plurality of signal cables partially overlap one another on the bendable circuit board.

By electrically connecting the plurality of signal cables in the state in which a plurality of signal cables partially overlap one another on the bendable circuit board, the wiring density of the signal cables is increased. Thereby, the imaging apparatus can be made more compact.

In the imaging apparatus according to the aspect of the present invention, it is preferable that the thixotropic ratio of the first resin is 1.5 or lower, and the thixotropic ratio of the second resin is 2.2 to 3.5.

In the imaging apparatus according to the aspect of the present invention, it is preferable that a viscosity of the first resin is 1 to 500 Pa·s, and a viscosity of the second resin is 100 to 500 Pa·s.

By setting the thixotropic ratio of the first resin to 1.5 or lower, occurrence of voids can be more effectively suppressed.

By setting the thixotropic ratio of the second resin to 2.2 to 3.5, the second resin can be more effectively prevented from flowing out from the connection part along the signal cable. Especially, by adopting the aforementioned range, the second resin has a certain degree of flowability, and therefore, when the plurality of signal cables are electrically connected in the state in which they partially overlap one another on the bendable circuit board, the second resin can reliably seal the connection part of the signal cable located at the lower side.

Here, as the value of the thixotropic ratio, the value which is defined by Ti (thixotropic ratio)=$\eta_2/\eta_{20}$ when $\eta_2$ (Pa·s) indicates the viscosity measured at a rotor speed of 2 rpm, and $\eta_{20}$ (Pa·s) indicates the viscosity measured at a rotor speed of 20 rpm, under an atmospheric temperature of 25° C.

As the value of the viscosity, the value obtained with a B type rotational viscometer at 23° C. at 2 rpm is used.

In the imaging apparatus according to the aspect of the present invention, it is preferable that the plurality of signal cables and the bendable circuit board are bent in a manner that the first resin and the second resin are disposed between parts of the bendable circuit board, and the first resin and the second resin are bonded and fixed to the bendable circuit board.

By bending the bendable circuit board, the imaging apparatus is made compact. Further, in the state in which the signal cables and the bendable circuit board are bent, the first resin and the second resin are bonded and fixed to the bendable circuit board.

Thereby, the bent form of the bendable circuit board can be held. Further, the external force which is applied to the connection part of the signal cables can be made small. Accordingly, breakage of the signal cables can be prevented.

The bending direction of the bendable circuit board may be a direction orthogonal to the signal cables, the direction parallel with the signal cables, or both of them. When the bendable circuit board is bent in the direction orthogonal to the signal cables, the external force applied to the signal cables is easily dispersed, and breakage of the connection part of the signal cables and the bendable circuit board can be more reliably prevented.

Further, the signal cables may be disposed at the mountain side of the bent bendable circuit board, or may be disposed at the valley side. Further, the connection position of the signal cables and the bendable circuit board may be on the same surface as the mounting surface of the electronic components mounted on the bendable circuit board, or may be on the opposite surface.

In the imaging apparatus according to the aspect of the present invention, it is preferable that the bonding and fixing is bonding and fixing by a third resin which has a thixotropic ratio higher than those of the first resin and the second resin, and has elasticity lower than those the first resin and the second resin.

By bonding and fixing with the third resin with a high thixotropic ratio, the third resin can be prevented from spreading to the portions which do not require the third resin. Further, by bonding and fixing with the third resin with low elasticity, the stress by the external force applied to the bendable circuit board and the signal cables can be relieved.

In the imaging apparatus according to the aspect of the present invention, it is preferable that the bonding and fixing is bonding and fixing by an adhesive tape. By performing bonding and fixing with an adhesive tape, the assembly process can be simplified.

In the imaging apparatus according to the aspect of the present invention, it is preferable that flattening treatment is applied to a top surface of at least one of the first resin and the second resin.

Especially when the bendable circuit board is bent, and the connection part of the plurality of signal cables and the electronic components are disposed between parts of the bendable circuit board, the first resin and the second resin and the bendable circuit board can be easily bonded and fixed by applying flattening treatment to the top surfaces of the first resin and the second resin.

In the imaging apparatus according to the aspect of the present invention, it is preferable that a permanent member or a shield member is provided on the top surface of at least one of the first resin and the second resin.

By providing the permanent member or the shield member on the top surfaces of the first resin and the second resin to which the flattening treatment is applied, overflow of the resin can be prevented, the form can be controlled, and the shield member can be caused to function as a shield.

In order to attain the above described object, an endoscope according to another aspect of the present invention includes the imaging apparatus according to the aspect which is disposed at a tip end portion of an insertion section of the endoscope. According to the aspect, the imaging apparatus is provided inside the tip end of the endoscope, and therefore, the endoscope with high physical and electrical reliability can be obtained.

According to the present invention, an imaging apparatus and an endoscope which can be made compact and have high physical and electrical reliability can be obtained.

BRIEF DESCRIPTION OF THE DRAWINGS

FIG. 2 is a sectional view of a tip end portion of an insertion section of an endoscope in which an imaging apparatus is incorporated.

DETAILED DESCRIPTION OF THE PREFERRED EMBODIMENTS

Hereinafter, a preferred embodiment of the present invention will be described in accordance with the accompanying drawings. The present invention is described according to the following preferable embodiment, but various modifications can be made by a number of methods without departing from the scope of the present invention, and embodiments other than the present embodiment can be used. Accordingly, all modifications within the scope of the present invention are included in claims.

Further, the numerical range expressed by using "to" in the present description means the range including the numerical values described before and after "to".

Figure 1:
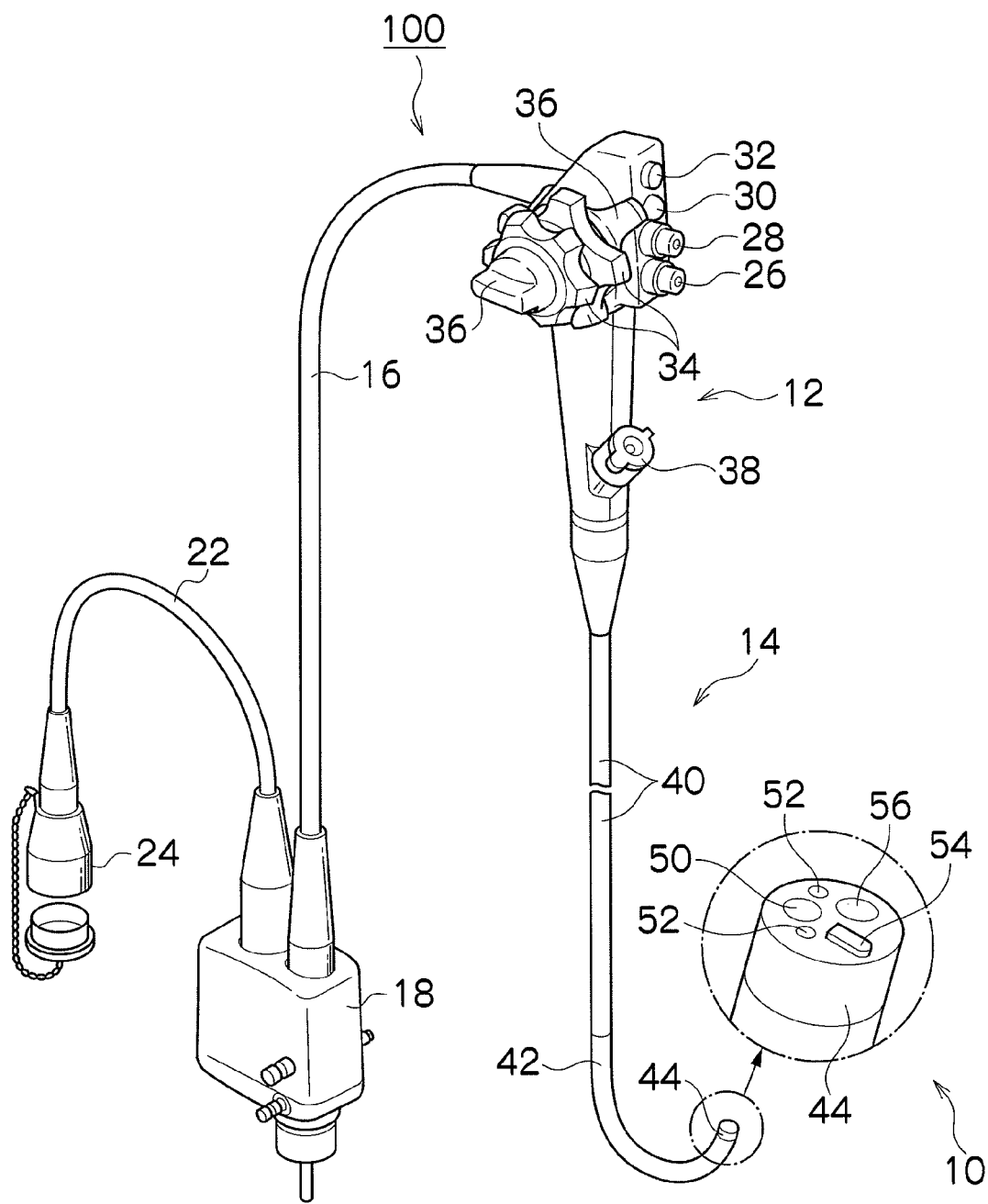
FIG. 1 is a perspective view showing an endoscope.

FIG. 1 is a perspective view showing an endoscope of the present embodiment. As shown in FIG. 1, an endoscope 100 includes a hand operating section 12, and an insertion section 14 provided connectively to the hand operating section 12. The hand operating section 12 is gripped by an operator, and the insertion section 14 is inserted into a body of a test subject.

A universal cable 16 is connected to the hand operating section 12, and an LG connector 18 is provided at a tip end of the universal cable 16. By attachably and detachably connecting the LG connector 18 to a light source device not illustrated, illumination light is sent to an illumination optical system 52 placed (arranged) at the tip end portion of the insertion section 14. An electric connector 24 is connected to the LG connector 18 through a cable 22, and the electric connector 24 is attachably and detachably connected to a processor not illustrated. Thereby, the data of the observation image obtained by the endoscope 100 is output to the processor, and the image is displayed on a monitor (not illustrated) which is further connected to the processor.

Further, on the hand operating section 12, an air supply/water supply button 26, a suction button 28, a shutter button 30 and a function switch button 32 are placed side by side. The air supply/water supply button 26 is an operation button for injecting air or water toward the observation optical system 50 from the air supply/water supply nozzle 54 placed at a tip end portion 44 of the insertion section 14, and the suction button 28 is an operation button for sucking a lesion portion or the like from a forceps port 56 placed at the tip end portion 44. The shutter button 30 is an operation button for operating recording or the like of the observation image, and the function switch button 32 is an operation button for switching the function or the like of the shutter button 30.

Further, a pair of angle knobs 34 and 34, and lock levers 36 and 36 are provided at the hand operating section 12. By operating the angle knob 34, a bending portion 42 which will be described later is operated to bend, and by operating the lock lever 36, fixing, and release of fixing of the angle knob 34 are operated.

Further, the hand operating section 12 is provided with a forceps insertion portion 38, and the forceps insertion portion 38 communicates into the forceps port 56 at the tip end portion 44. Accordingly, by inserting an endoscope treatment instrument such as forceps (not illustrated) from the forceps insertion portion 38, the endoscope treatment instrument can be guided out from the forceps port 56.

Meanwhile, the insertion section 14 includes a flexible portion 40, the bending portion 42 and the tip end portion 44 in sequence from the hand operating section 12 side. The flexible portion 40 has flexibility, and is configured by applying coating such as a resin onto a core material formed of a metal net tube or a helix tube of a metal plate.

The bending portion 42 is configured to be bent remotely by turning the angle knobs 34 and 34. For example, the bending portion 42 is made by rotatably (turnably) connecting a plurality of cylindrical joint rings (not illustrate) by a guide pin (not illustrated), and a plurality of operation wires (not illustrated) are inserted into the joint rings to guide the cylindrical joint rings by the guide pin. The operation wires are inserted through the flexible portion 40 of the insertion section 14 in the state in which the operation wires are inserted through a contact coil, and connected to the angle knobs 34 and 34 of the hand operating section 12 through a pulley (not illustrated) or the like. Accordingly, the operation wires are operated to be pushed and pulled by operating the angle knobs 34 and 34, the joint rings (not illustrated) are turned, and the bending portion 42 is operated to bend.

On the tip end surface (side surface in the case of the side looking endoscope) of the tip end portion 44, the observation optical system (observation lens) 50, the illumination optical system (illumination lens) 52, the air supply/water supply nozzle 54, the forceps port 56 and the like are provided.

The illumination optical system 52 is provided adjacently to the observation optical system 50, and the illumination optical systems 52 are disposed at both sides of the observation optical system 50 in accordance with necessity. In the interior of the illumination optical system 52, an exit end of the light guide (not illustrated) is placed. The light guide is inserted through the insertion section 14, the hand operating section 12 and the universal cable 16, and an incident end of the light guide is disposed inside the LG connector 18. Accordingly, by connecting the LG connector 18 to a light source device (not illustrated), illumination light irradiated from the light source device is transmitted to the illumination optical system 52 through the light guide, and is irradiated to the observation range in front from the illumination optical system 52.

The air supply/water supply nozzle 54 is opened toward the observation optical system 50, and an air supply/water supply tube (not illustrated) is connected to the air supply/water supply nozzle 54. The air supply/water supply tube is inserted through the insertion section 14, and after being branched halfway, the air supply/water supply tube is connected to an air supply/water supply valve (not illustrated) in the hand operating section 12. The air supply/water supply valve is operated by the air supply/water supply button 26, and thereby, air or water is injected toward the observation optical system 50 from the air supply/water supply nozzle 54.

A tube-shaped forceps channel 58 (see FIG. 2) is connected to the forceps port 56, and the forceps channel 58 is inserted through the interior of the insertion section 14. After the forceps channel 58 is branched, one of the branches is inserted through the forceps insertion portion 38 at the hand operating section 12, and the other of the branches is connected to a suction valve (not illustrated) in the hand operating section 12. The suction valve is operated by the suction button 28, and thereby, a lesion portion and the like can be sucked from the forceps port 56. The forceps port 56, the forceps channel 58 and the like are provided in accordance with necessity, and may be omitted, for example, in the case of a nasal endoscope and the like.

FIG. 2 shows a section of the tip end portion 44 of the insertion section 14. As shown in FIG. 2, the imaging apparatus 10 is disposed at the tip end portion 44. The observation optical system 50 includes a lens 68, a lens barrel 69, a prism 70 and the like, and is fixed in the state inserted through a main body 60. The main body 60 is formed into a substantially columnar shape by a metal or the like, and a resin cap 62 is mounted to the tip end side of the main body 60. Further, a tip end sleeve 64 of the bending portion 42 is fitted onto the main body 60, and a periphery of the tip end sleeve 64 is covered with a coating member 66.

A solid state imaging element 72 such as a CCD and CMOS is attached to the prism 70 of the observation optical system 50. A flexible board 74 with flexibility is connected to the solid state imaging element 72, and a large number of signal cables 78 (also called cable conductors) for signal transfer are electrically connected to the flexible board 74. Each of the signal cables 78 is configured by covering the core wire with coating, and the plurality of signal cables 78 are coated with a coating 76 in the state in which they are bundled. The signal cables 78 are inserted into the insertion section 14, the universal cable 16 and the like as a multicore cable, extend to the electric connector 24, and is connected to the processor (not illustrated). Accordingly, the observational image taken in by the observation optical system 50 is formed on the light receiving surface of the solid state imaging element 72 to be converted into an electrical signal, and thereafter, the signal is output to the processor through the signal cables 78 to be converted into a video signal. Thereby, the observational image is displayed on the monitor connected to the processor.

In the present embodiment, a plurality of electronic components 82 are sealed with a first resin 90. The first resin 90 has a thixotropic ratio of 1.5 or lower, and a viscosity of 1 to 500 Pa·s. The first resin 90 has a low thixotropic ratio and therefore, has high flowability. Thereby, when a plurality of electronic components are sealed, the resin can be prevented from being unfilled, and occurrence of voids can be reduced. Accordingly, the problem which occurs when voids occur to the first resin 90, for example, release of the electronic components due to expansion of air in the voids at a time of high temperature, and corrosion accompanying entry of vapor into the voids can be prevented.

By setting Tg (glass transition temperature) of the first resin 90 at 60° C. or higher which is the use temperature of the endoscope, physical (mechanical)/electrical protection of the imaging apparatus 10 is ensured.

As the first resin 90, a thermosetting epoxy resin can be used. An epoxy resin includes an inorganic filler of silica, alumina or the like for the purpose of reducing the rate of moisture absorption, reducing a thermal expansion coefficient and increasing thermal conductivity. Further, the first resin includes a filler and impalpable powder of silica, alumina, asbestos, organic fiber, calcium carbonate and the like as a thixotropic agent for controlling thixotropy. As the epoxy resin, bisphenol A epoxy, bisphenol B epoxy, cycloaliphatic epoxy and the like can be used.

In the present embodiment, the plurality of signal cables 78 are electrically connected to a land formed along a longitudinal direction of the flexible board 74, on the flexible board 74, by solder or the like. Thereby, the plurality of signal cables 78 are electrically connected to the flexible board 74 in the state in which the plurality of signal cables 78 partially overlap one another in the vertical direction on the flexible board 74.

Generally, the signal cable 78 is coated, and has a structure which easily repels a resin. Further, a plurality of signal cables 78 are bundled, and therefore, they have the structure which easily causes a resin to flow out by capillarity when sealed with the resin.

In the present embodiment, a connection part of a plurality of signal cables 78 and the flexible board 74 are sealed with a second resin 92. The second resin 92 has a thixotropic ratio of 2.2 to 3.5, and a viscosity of 100 to 500 Pa·s. The second resin 92 has a relatively high thixotropic ratio, and therefore, has flowability suppressed. Thereby, the second resin 92 can be effectively prevented from flowing out from the connection part along the signal cables 78.

Meanwhile, the thixotropic ratio of the second resin 92 is not too high, and therefore, the second resin 92 has a certain degree of flowability. Thereby, the connection part of the signal cables 78 which is located at a lower side of the plurality of signal cables 78 disposed to overlap one another vertically can be reliably sealed. Further, voids can be prevented from occurring to the second resin 92.

Further, Tg (glass transition temperature) of the second resin 92 is set to 60° C. or more which is the use temperature of the endoscope, and thereby, physical (mechanical) and electrical protection of the imaging apparatus 10 is ensured.

As the second resin 92, a thermosetting epoxy resin can be used. An epoxy resin includes an inorganic filler of silica, alumina or the like for the purpose of reducing the rate of moisture absorption, reducing a thermal expansion coefficient and increasing thermal conductivity and the like. Further, the epoxy resin includes a filler and impalpable powder of silica, alumina, asbestos, organic fiber, calcium carbonate and the like as a thixotropic agent for controlling thixotropy. As the epoxy resin, bisphenol A epoxy, bisphenol B epoxy, cycloaliphatic epoxy and the like can be used.

The flexible board 74 is bent at two spots with a direction orthogonal to the signal cables 78 as the center. Thereby, the flexible board 74 is bent into an S-shape. The number of bends and the bending directions of the flexible board 74 are not limited to the above described embodiment.

By bending the flexible board 74, the electronic components 82 and the first resin 90 are disposed between parts of the flexible board 74. Similarly, the connection part of the signal cables 78 and the second resin 92 are disposed between parts of the flexible board 74. Thereby, the imaging apparatus 10 can be made compact.

In order to keep the bent form (S-shape) of the flexible board 74, the first resin 90 and the second resin 92 are bonded and fixed by a third resin 94. The third resin 94 preferably has a thixotropic ratio of 2.2 or higher, and more preferably three or higher. Further, the third resin 94 preferably has a viscosity of 10 to 500 Pa·s. Its modulus of elasticity is small as compared with those of the first resin 90 and the second resin 92, and the glass transition temperature of the third resin 94 is preferably Tg 45° C. or lower.

By bonding and fixing with the third resin 94 with a high thixotropic ratio, the third resin 94 can be prevented from spreading to a portion which does not require the third resin 94. Further, by bonding and fixing with the third resin 94 having a low elasticity, stress by external force, which is applied to the bendable circuit board and signal cables, can be relieved.

Further, by setting Tg (glass transition temperature) of the third resin 94 at 60° C. or higher which is the use temperature of an endoscope, physical (mechanical) and electrical protection of the imaging apparatus 10 is ensured.

As the third resin 94, a thermosetting epoxy resin can be used. An epoxy resin includes an inorganic filler of silica, alumina or the like for the purpose of reducing the moisture absorption amount, reducing the thermal expansion coefficient and increasing thermal conductivity. Further, the epoxy resin includes a filler and impalpable powder of silica, alumina, asbestos, organic fiber, calcium carbonate or the like as a thixotropic agent for controlling thixotropy. As the epoxy resin, bisphenol A epoxy, bisphenol B epoxy, cycloaliphatic epoxy and the like can be used.

The main components of the first resin 90, the second resin 92 and the third resin 94 are the same, and their properties are controlled by the kind of additives.

Hereinafter, a manufacturing method of the imaging apparatus 10 will be described. The same reference numerals and characters will be assigned to the same components as those already described in FIGS. 1 and 2, and the description of them may be omitted.

Figure 3A:
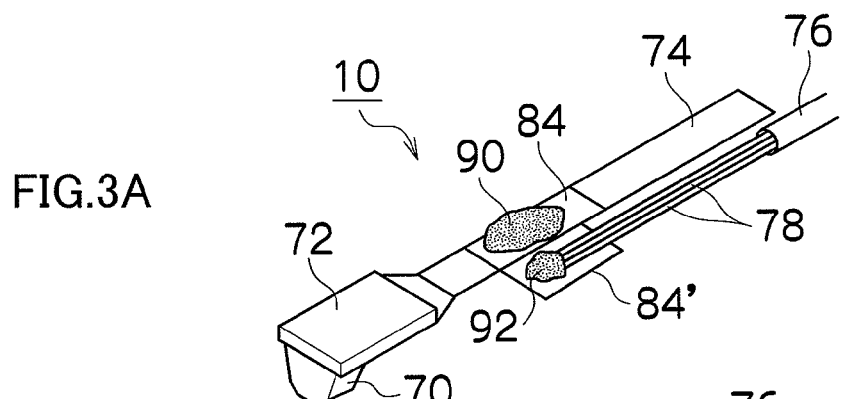
FIGS. 3A to 3D are explanatory views explaining a manufacturing method of the imaging apparatus.

FIGS. 3A to 3D schematically show the manufacturing method of the imaging apparatus 10. FIG. 3A shows the flexible board 74 before being bent. As shown in FIG. 3A, the solid state imaging element 72 is connected to the tip end of the flexible board 74. The prism 70 is disposed at the light receiving surface side of the solid state imaging element 72.

The flexible board 74 is configured by sandwiching a conductive member of a copper foil or the like to be a wiring pattern by an insulative resin film such as a polyimide film and a PET film, and by coating it with a solder resist and performing patterning. The flexible board 74 is thin in thickness and flexible, and therefore, can be easily bent.

Electronic components (IC, resistors, capacitors, transistors and the like) (not illustrated) are mounted on a mounting part 84 on one side surface of the flexible board 74. The electronic components are sealed by the first resin 90 which is an epoxy resin. The first resin 90 is supplied by a dispenser, for example. Thereafter, the first resin 90 is hardened under the conditions at 100° C. to 150° C. and for about four hours.

A mounting part 84' for electrically connecting the signal cables 78 and the flexible board 74 is formed on the same surface side as the mounting part 84 in a protruding manner from the flexible board 74. The signal cables 78 and the flexible board 74 are electrically connected on the mounting part 84' of the flexible board 74.

Figure 3B:
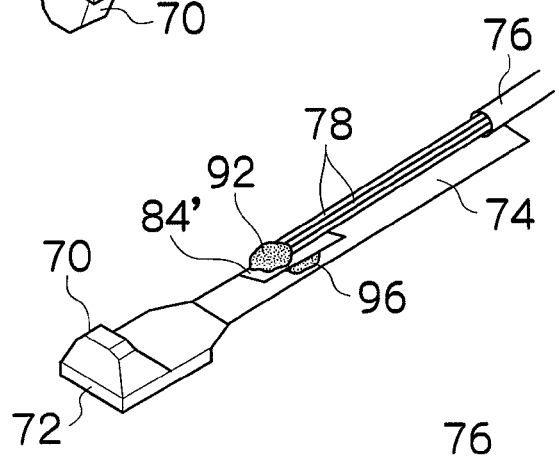

The connection part of the signal cables 78 and the flexible board 74 is sealed by the second resin 92 which is an epoxy resin. The second resin 92 is supplied by a dispenser, for example. Thereafter, the second resin 92 is hardened under the conditions at 100° C. and for about 0.5 hours. Next, as shown in FIG. 3B, the imaging apparatus 10 is inverted so that the prism 70 is located on the upper side. The mounting part 84' is folded back so that the mounting part 84' for the signal cables 78 is located on an opposite surface with respect to the mounting part 84 of the electronic components with the flexible board 74 therebetween. The mounting part 84' and the flexible board 74 are bonded and fixed by an adhesive agent 96.

Figure 3C:
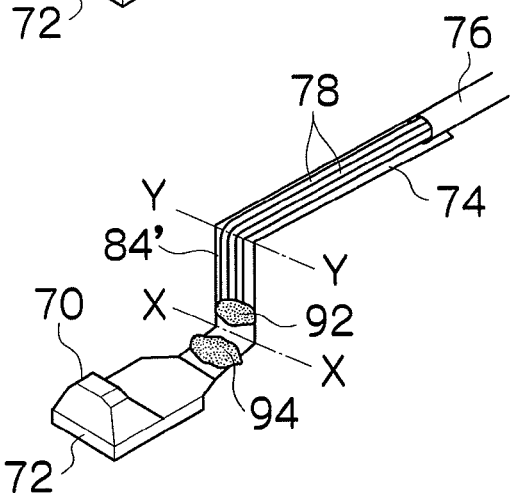

Next, as shown in FIG. 3C, the flexible board 74 is bent at two positions along an X-X line direction and a Y-Y line direction which are the directions orthogonal to the signal cables 78 as the centers. By bending the flexible board 74, the signal cables 78 are bent at the same time. In the present embodiment, the signal cables 78 are bent in the mountain side (outside) of a bending position Y.

Between the two bending positions X and Y, the mounting part 84, and the connection part of the signal cables 78 and the flexible board 74 are located between parts of the flexible board 74.

In the present embodiment, a third resin 94 is provided on a top surface of the flexible board 74 located at the position opposed to the second resin 92. By the third resin 94, the second resin 92 and the flexible board 74 are bonded and fixed.

Figure 3D:
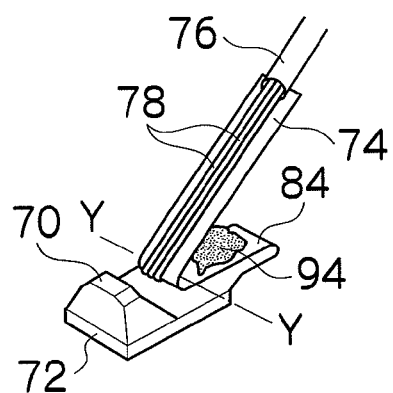

Next, as shown in FIG. 3D, after the flexible board 74 is bent at X, the flexible board 74 is further bent at Y. The third resin 94 is provided on a top surface of the first resin 90. The flexible board 74 is bent to be parallel with the mounting part 84. The flexible board 74 and the first resin 90 are bonded and fixed by the third resin 94. By the third resin 94, the first resin 90 and the second resin are bonded and fixed to the flexible board 74, and therefore, the flexible board 74 can keep the bent state (S-shaped form).

In the present embodiment, the signal cables 78 are disposed at the mountain side (outside) of the flexible board 74 with respect to the bending position, but may be disposed at the valley side (inside).

Next, a method of flattening the first resin and the second resin will be described with reference to FIGS. 4A to 4C. The same components as those already described in FIG. 1 to FIGS. 3A to 3D will be assigned with the same reference numerals and characters, and description of them may be omitted.

Figure 4A:
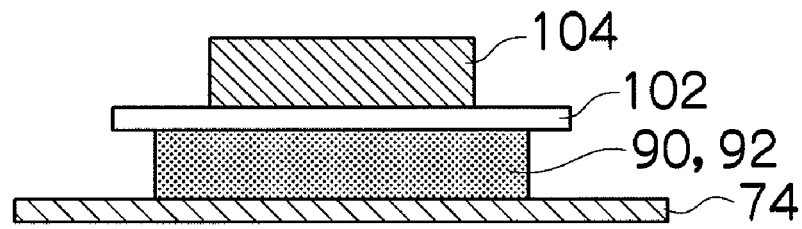
FIGS. 4A to 4C are explanatory views explaining part of another manufacturing method of the imaging apparatus.

As shown in FIG. 4A, the first resin 90 for sealing the electronic components or the second resin 92 for sealing the connection part of the signal cables are supplied onto the flexible board 74 from a dispenser (not illustrated). Before the resins are thermally cured, a release member 102 in a flat plate shape is placed on the top surface of the first resin 90 or the second resin 92. Further, a weight 104 is placed on the release member 102, and the first resin 90 or the second resin 92 is cured under predetermined curing conditions.

Figure 4B:
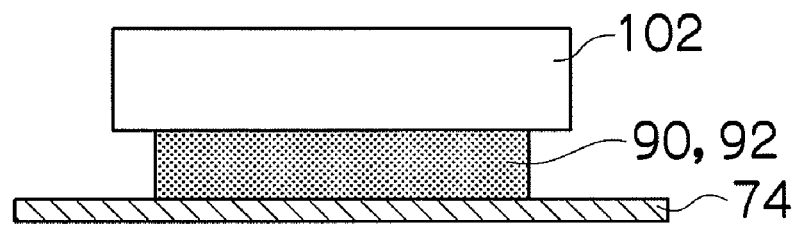
Figure 4C:
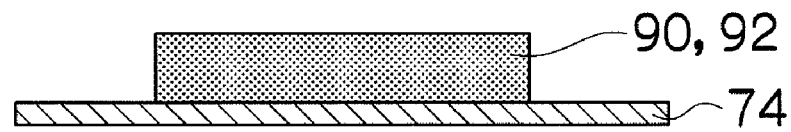

Next, by removing the release member 102 and the weight 104, the top surface of the first resin 90 or the second resin 92 can be flattened as shown in FIG. 4C.

Further, as another method, as shown in FIG. 4B, the release member 102 with a flat undersurface which is also used as a weight is placed on the top surface of the first resin 90 or the second resin 92 before the resins are thermally cured. Next, under predetermined curing conditions, the first resin 90 or the second resin 92 is cured. By removing the release member 102, the top surface of the first resin 90 or the second resin 92 can be flattened as shown in FIG. 4C.

By flattening the top surface of the first resin 90 or the second resin 92, an adhesive tape such as a double-sided adhesive tape can be used instead of the third resin 94 when the flexible board 74 and the first resin 90 or the second resin 92 are bonded and fixed by bending the flexible board 74 as shown in FIGS. 3A to 3D. For the flat surface of the first resin 90 or the second resin 92 and the flat surface of the flexible board 74, adhesive force can be ensured even with an adhesive tape.

Next, an application example in the case where the first resin and the second resin are flattened will be described with reference to FIGS. 5A to 5C.

Figure 5A:
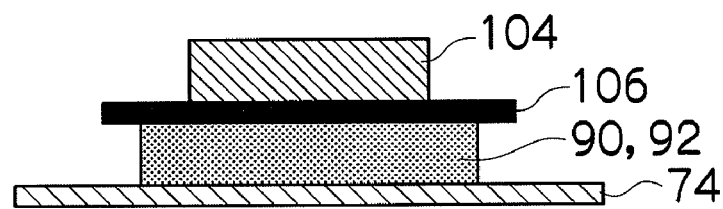
FIGS. 5A to 5C are explanatory views explaining part of still another manufacturing method of the imaging apparatus, and a section of the imaging apparatus.

As shown in FIG. 5A, the first resin 90 for sealing the electronic components or the second resin 92 for sealing the connection part of the signal cable is supplied onto the flexible board 74 from a dispenser (not illustrated). Before the resins are thermally cured, a member 106 in a flat plate shape is placed on the top surface of the first resin 90 or the second resin 92. As the member 106, a permanent member of polyimide or the like, or a shield member of a copper foil or the like is used. Further, the weight 104 is placed on the member 106, and the first resin 90 or the second resin 92 is cured under the predetermined curing conditions.

Figure 5B:

Next, by removing only the weight 104, the member 106 can be left on the flattened top surface of the first resin 90 or the second resin 92 as shown in FIG. 5B.

Figure 5C:
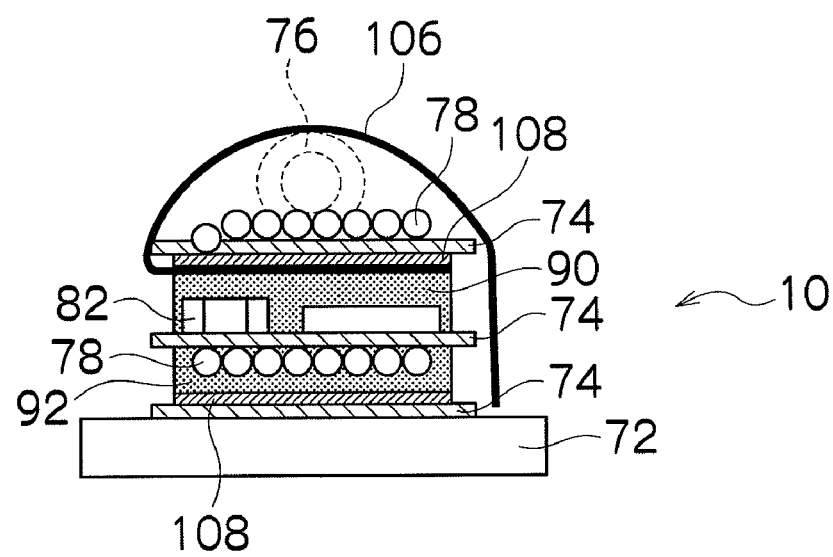

By extending the member 106, which is left on the flattened resin top surface, to be long, the entire imaging apparatus 10 can be covered as shown in FIG. 5C.

FIG. 5C is a sectional view of the imaging apparatus 10 along a line orthogonal to the flexible board 74. The flexible board 74 is electrically connected to the solid state imaging element 72. The flexible board 74 is bent into an S-shape as shown in FIGS. 3A to 3D. Accordingly, the flexible board 74 has a three-story structure on the solid state imaging element 72. The signal cables 78 and the second resin 92 are disposed between the lowermost part of the flexible board 74 and the central part of the flexible board 74. Further, the electronic components 82 and the first resin 90 are disposed between the central part of the flexible board 74 and the uppermost part of the flexible board 74.

In the present embodiment, the member 106 is placed on the flattened top surface of the first resin 90. The member 106 is extended to be long in the width direction of the flexible board 74. The member 106 is bent in the upward direction to cover the signal cables 78 and the coating 76 disposed on the uppermost part of the flexible board 74. Finally, the member 106 is bent so that one end of it is located near the solid state imaging element 72.

For example, when a shield member is adopted as the member 106 in the aforementioned configuration, the imaging apparatus 10 can be shield by the member 106. When a permanent member is adopted as the member 106, the shape of the flexible board 74 can be held more efficiently. Further, the member 106 can be caused to function as a retaining mold which prevents the third resin (not illustrated) which bonds and fixes the first resin 90, the second resin 92 and the flexible board 74 from flowing out.

The first resin 90 and the second resin 92 have the flattened top surfaces, and therefore, the first resin 90, the second resin 92 and the flexible board 74 can be fixed with the double-sided adhesive tape 108. By using the double-sided adhesive tape 108 of an acrylic material, concentration of stress can be prevented. Further, assembly can be simplified.

In the present embodiment, the flexible board is described as an example of the bendable circuit board, but the bendable circuit board is not limited to this, and a composite circuit board using a rigid board such as a glass epoxy board and a flexible board in combination can be used if only the board is bendable.

What is claimed is:

1. An imaging apparatus, comprising:
   an observation optical system;
   a solid state imaging element which photoelectrically converts an image from the observation optical system;
   a bendable circuit board electrically connected to the solid state imaging element;
   a plurality of electronic components and a plurality of signal cables electrically connected to the bendable circuit board;
   a first resin which seals the electronic components; and
   a second resin which seals a connection part of the signal cables, the second resin having a thixotropic ratio which is higher than a thixotropic ratio of the first resin.

2. The imaging apparatus according to claim 1,
   wherein the plurality of signal cables are connected to the bendable circuit board in a state in which the plurality of signal cables partially overlap one another on the bendable circuit board.

3. The imaging apparatus according to claim 1,
   wherein the thixotropic ratio of the first resin is 1.5 or lower, and the thixotropic ratio of the second resin is 2.2 to 3.5.

4. The imaging apparatus according to claim 1,
   wherein a viscosity of the first resin is 1 to 500 Pa·s, and a viscosity of the second resin is 100 to 500 Pa·s.

5. The imaging apparatus according to claim 1,
   wherein the plurality of signal cables and the bendable circuit board are bent in a manner that the first resin and the second resin are disposed between parts of the bendable circuit board, and the first resin and the second resin are bonded and fixed to the bendable circuit board.

6. The imaging apparatus according to claim 5,
   wherein the bonding and fixing is bonding and fixing by a third resin which has a thixotropic ratio higher than those of the first resin and the second resin, and has elasticity lower than those the first resin and the second resin.

7. The imaging apparatus according to claim 5,
   wherein the bonding and fixing is bonding and fixing by an adhesive tape.

8. The imaging apparatus according to claim 5,
   wherein flattening treatment is applied to a top surface of at least one of the first resin and the second resin.

9. The imaging apparatus according to claim 8,
   wherein a permanent member or a shield member is provided on the top surface of at least one of the first resin and the second resin.

10. An endoscope, comprising
    the imaging apparatus according to claim 1 disposed at a tip end portion of an insertion section of the endoscope.

* * * * *